United States Patent
Taghipour

(10) Patent No.: US 10,293,072 B2
(45) Date of Patent: May 21, 2019

(54) AIR PURIFIER FOR TRANSPORTATION VEHICLES

(71) Applicant: Fariborz Taghipour, Burnaby (CA)

(72) Inventor: Fariborz Taghipour, Burnaby (CA)

( * ) Notice: Subject to any disclaimer, the term of this patent is extended or adjusted under 35 U.S.C. 154(b) by 0 days.

(21) Appl. No.: 15/064,548

(22) Filed: Mar. 8, 2016

(65) Prior Publication Data
US 2016/0256590 A1      Sep. 8, 2016

Related U.S. Application Data

(63) Continuation of application No. 14/467,676, filed on Aug. 25, 2014, now abandoned.
(60) Provisional application No. 61/872,742, filed on Sep. 1, 2013.

(51) Int. Cl.
*A61L 9/20* (2006.01)
*B64D 13/06* (2006.01)

(52) U.S. Cl.
CPC .............. *A61L 9/205* (2013.01); *B64D 13/06* (2013.01); *B64D 2013/0651* (2013.01); *B64D 2013/0688* (2013.01)

(58) Field of Classification Search
None
See application file for complete search history.

(56) References Cited

U.S. PATENT DOCUMENTS

| | | | |
|---|---|---|---|
| 3,893,829 A * | 7/1975 | Valentino | B01D 47/06 261/35 |
| 4,210,428 A * | 7/1980 | Schneider | B01D 47/06 261/116 |
| 5,696,380 A | 12/1997 | Cooke et al. | |
| 5,919,422 A * | 7/1999 | Yamanaka | A61L 2/232 422/121 |
| 6,403,030 B1 * | 6/2002 | Horton, III | A61L 2/10 210/748.11 |
| 6,447,720 B1 * | 9/2002 | Horton, III | A61L 2/10 210/748.11 |
| 6,454,937 B1 | 9/2002 | Horton et al. | |
| 6,803,586 B1 | 10/2004 | Brunet et al. | |

(Continued)

FOREIGN PATENT DOCUMENTS

| | | |
|---|---|---|
| DE | 102010047318 A1 | 4/2012 |
| WO | 2009013507 A1 | 1/2009 |

(Continued)

OTHER PUBLICATIONS

Ducoste, Joel et al. "Hydrodynamic Characterization of UV Reactors." North Carolina State University, Raleigh, NC 27695-7908. Available online at http://www.waterrf.org/PublicReportLibrary/2682.pdf. 2006.

(Continued)

*Primary Examiner* — Krishnan S Menon
*Assistant Examiner* — Bradley R Spies
(74) *Attorney, Agent, or Firm* — Todd A. Rattray, Oyen Wiggs Green & Mutala LLP

(57) ABSTRACT

A vehicle air purification system has a photocatalyst activated by photons emitted via an ultraviolet light emitting diode (UV-LED). The photocatalyst on a supporting structure is positioned to contact airflow passing through or over the photocatalyst. Chemical contaminants and microorganisms are eliminated from the airflow that makes contact with the photocatalyst structure.

22 Claims, 16 Drawing Sheets

(56) References Cited

U.S. PATENT DOCUMENTS

| | | |
|---|---|---|
| 6,940,075 B2 | 9/2005 | Schulz |
| 6,972,415 B2 | 12/2005 | Schaible et al. |
| 7,309,409 B2 | 12/2007 | Amirkhanian et al. |
| 7,408,174 B2 | 8/2008 | From et al. |
| 7,498,004 B2 | 3/2009 | Saccomanno |
| 7,641,790 B2 | 1/2010 | Maiden |
| 7,862,728 B2 | 1/2011 | Yencho |
| 7,910,899 B2 | 3/2011 | Platsch |
| 8,088,289 B2 | 1/2012 | Tribelsky |
| 8,322,199 B2 | 12/2012 | Reed |
| 8,324,595 B2 | 12/2012 | Takahashi et al. |
| 8,420,022 B2 | 4/2013 | Soler et al. |
| 8,444,918 B2 | 5/2013 | Tanaka |
| 8,506,886 B2 | 8/2013 | Owen et al. |
| 8,673,218 B2 | 3/2014 | Jaffe et al. |
| 8,722,396 B2 | 5/2014 | Kassebaum et al. |
| 9,044,521 B2 | 6/2015 | Farren |
| 9,174,858 B2 | 11/2015 | Ma et al. |
| 2002/0080615 A1 | 6/2002 | Marshall et al. |
| 2002/0144955 A1 | 10/2002 | Barak et al. |
| 2004/0103790 A1* | 6/2004 | Yang .............. B01D 46/0028 96/224 |
| 2005/0242013 A1 | 11/2005 | Hunter et al. |
| 2006/0131246 A1 | 6/2006 | Ehlers, Sr. |
| 2006/0283786 A1 | 12/2006 | Harbers |
| 2007/0099292 A1 | 5/2007 | Miller et al. |
| 2008/0003171 A1* | 1/2008 | Smith .................. A01N 59/00 423/473 |
| 2008/0225528 A1 | 9/2008 | Holder et al. |
| 2008/0286163 A1 | 11/2008 | Garfield et al. |
| 2009/0084734 A1* | 4/2009 | Yencho ................ C02F 1/325 210/741 |
| 2009/0230038 A1 | 9/2009 | Tanaka et al. |
| 2010/0237254 A1 | 9/2010 | Mason et al. |
| 2010/0291502 A1 | 11/2010 | Knight |
| 2011/0291995 A1 | 10/2011 | Stir et al. |
| 2012/0070335 A1 | 3/2012 | Carey |
| 2012/0076700 A1* | 3/2012 | Liptak ................. A61L 9/205 422/186.3 |
| 2012/0128539 A1* | 5/2012 | Gross ................... A61L 9/205 422/121 |
| 2012/0138545 A1* | 6/2012 | Soler .................... C02F 1/325 210/748.16 |
| 2012/0171079 A1* | 7/2012 | Morito ................. A61L 2/088 422/121 |
| 2012/0298592 A1 | 11/2012 | Boal et al. |
| 2013/0236353 A1 | 9/2013 | Blechschmidt et al. |
| 2014/0202962 A1 | 7/2014 | Bilenko et al. |
| 2015/0008167 A1 | 1/2015 | Shturm et al. |
| 2015/0064069 A1 | 3/2015 | Yi et al. |
| 2015/0129776 A1 | 5/2015 | Boodaghians et al. |
| 2015/0144575 A1 | 5/2015 | Hawkins, II |
| 2015/0158741 A1 | 6/2015 | Lee et al. |

FOREIGN PATENT DOCUMENTS

| | | |
|---|---|---|
| WO | 2011092541 A1 | 8/2011 |
| WO | 2012010645 A1 | 1/2012 |
| WO | 2015000756 A1 | 1/2015 |

OTHER PUBLICATIONS

Flis, Kevin. "Development of an inclined orientation UV system permits smaller footprints." Available online at http://c.ymcdn.com/sites/www.ncsafewater.org/resource/collection/DA8375FB-1514-4325-9CF6-0369B08C4385/WW_Tues_PM_03.20_Flis_PAPER.pdf. 2014.

Gandhi, V. "Visualization and quantification of hydrodynamics and dose in UV reactors by 3D laser-induced fluorescence". Georgia Institute of Technology. Available online at https://smartech.gatech.edu/bitstream/handle/1853/45895/gandhi_varun_n_201212_phd.pdf. Dec. 2012.

Jenny, Richard Matthew. "Numerical Optimization and Experimental Validation of a Continuous Flow Point-of-Use UV-LED Disinfection Reactor using Computational Fluid Dynamics." North Carolina State University, Raleigh, North Carolina. Available online at http://repository.lib.ncsu.edu/ir/bitstream/1840.16/9498/1/etd.pdf. 2014.

Jenny, Richard M. et al. "Heuristic optimization of a continuous flow point-of-use UV-LED disinfection reactor using computational fluid dynamics." Water Research 83 (Jun. 23, 2015): 310-318.

Jenny, Richard M. et al. "Modeling a continuous flow ultraviolet Light Emitting Diode reactor using computational Fluid dynamics." Chemical Engineering Sciences 116 (May 28, 2014): 524-535.

Saha, Rajib Kumar. "Numerical Simulation of an Open Channel Ultraviolet Waste-water Disinfection Reactor." The University of Western Ontario, London Ontario, Canada. Available online at http://ir.lib.uwo.ca/cgi/viewcontent.cgi?article=2937&context=etd. Aug. 2013.

M. Kneissl, T. Kolbe, M. Würtele, E. Hoa (2010) Development of UV-LED disinfection, Techneau, 2010.

Oguma K., Kita R., Sakai H., Murakami M., Takizawa S. (2013) Application of UV light emitting diodes to batch and flow-through water disinfection systems, Desalination 328, 24-30.

Richard M. Jenny, Micah N. Jaspera, Otto D. Simmons IIIb, Max Shatalovc, Joel J. Ducostea (2015), Heuristic optimization of a continuous flow point-of-use UV-LED disinfection reactor using computational fluid dynamics, Water Research 83, 310-318.

Mukherjee et al., Major Challenges in the Design of a Large-Scale Photocatalytic Reactor for Water Treatment, 1999, pp. 253-260.

* cited by examiner

210

AIR PURIFIER FOR TRANSPORTATION VEHICLES

CROSS-REFERENCE TO RELATED APPLICATIONS

This application is a continuation of U.S. application Ser. No. 14/467,676, filed 25 Aug. 2014, which in turn claims priority, and the benefit under 35 USC 119(e), from U.S. Provisional Application No. 61/872,742, filed 1 Sep. 2013. The disclosures of U.S. application Ser. Nos. 14/467,676 and 61/872,742 are hereby incorporated herein by reference.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

The present invention relates to air purification systems, and more particularly, to an air purification system for transportation vehicles using ultraviolet (UV) activated photocatalyst for the degradation of chemical pollutants and elimination of microorganisms.

Advanced air purification systems can be applied to a wide range of purposes, from homes and offices to high-specification environments such as hospitals, laboratories, and industrial facilities. Ultraviolet (UV) photolysis and photocatalysis have been proved to be very effective for the elimination of many toxic airborne contaminants; and as a result have been incorporated in some high-end air purification systems. UV photocatalysis is being referred to as oxidation and reduction reactions on photocatalyst surfaces, which are generated by UV radiation. A photocatalyst is a substance that generates catalyst activity using radiation energy. A fundamental barrier to UV photocatalysis widespread deployment and application is the source for the UV radiation. The radiation source is UV lamps, which are relatively bulky, require high power, and have health and environmental issues due to the mercury contained in them. Furthermore, the UV lamps are typically needed replacing on a regular basis, leading to high maintenance costs. Such size, power, and cost considerations have excluded UV photocatalysis systems from a number of potential applications, which require a compact and low-power solution, for example in vehicle air purification systems.

Light emitting diodes (LEDs) emit radiation of a single wavelength. With recent advancements in LED technology, LEDs now can be designed to generate UV radiation. The UV-LEDs compact and robust design makes them an attractive alternative for replacing UV lamps in UV reactor systems.

There are harmful airborne contaminants and toxic organic chemicals within vehicles. A compact, low-power vehicular air purification system to eliminate chemical contaminants is desirable to vehicle users and manufacturers.

SUMMARY OF THE INVENTION

In one aspect, the present invention is a vehicle air purifying system operating with one or more ultraviolet light emitting diodes (UV-LEDs) that activates one or more photocatalyst structures, in order to kill microorganisms (e.g. bacteria and viruses) and to degrade chemical contaminants (e.g. toxic organic compounds). The UV-LED is arranged to emit ultraviolet (UV) radiation onto the photocatalyst structure. The photocatalyst structure is positioned to contact airflow passing through or over the photocatalyst structure. As used throughout this specification, the term "photocatalyst structure" is intended to mean a photocatalyst, a photocatalyst composition, or a photocatalyst supported on a substrate.

In another aspect, the present invention is a method of purifying airflow in transportation vehicles, comprising passing the airflow through a reactor including one or more photocatalyst structures; emitting ultraviolet radiation from one or more ultraviolet light emitting diodes (UV-LEDs) onto the photocatalyst structure; and eliminating chemical contaminants and microorganisms from the airflow that makes contact with the UV-activated photocatalyst structure while the photocatalyst is activated by the ultraviolet radiation emitted from the UV-LED.

These and other features, aspects, and advantages of the present invention will become better understood with reference to the following drawings, description, and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

In general, the present invention provides an air purifying system that eliminates chemical contaminants from airflow using a photocatalyst activated by UV radiation from a UV-LED. The airflow moves through the system by forced-convection preferably using an air-moving device such as an electrical fan. The photocatalyst is preferably supported on a porous substrate, where air passes through; or the photocatalyst is immobilized on a solid substrate, where air passes over. The photocatalyst may be titanium dioxide $TiO_2$, or other photocatalysts. It may also be any combination of photocatalysts and catalyst supports, and co-catalysts (such as metals and metal oxides).

The air purifying system may contain baffles or static mixers to alter the hydrodynamics of the airflow. This may be applied to provide a better distribution of the air through or over the photocatalyst and to enhance mass transfer of chemical contaminants to and from the photocatalyst surface. This may also be applied to provide a better thermal management of the system by transferring heat from the UV-LED and other parts of the air purifying system. Other material such as a heat sink or thermal conductive plates may also be applied to better transfer heat from the system. The air purifying system may also contain an air quality sensor to monitor and potentially indicate the air quality. A signal from the sensor may be used to turn the air purifying system on and off automatically.

The air purifying system may have the shape of a cylinder and the like that can be placed in a vehicle cup holder. It may also have the shape of a coffee tumbler, cup, or other typical drinking containers. The air purifying system may be powered by a vehicle electrical circuit, by a vehicle cabin power-outlet, or by a battery.

The air purifying system may be a mobile stand-alone reactor to be placed inside a transportation vehicle passenger cabin. Alternatively, the air purifying system may be integrated into the air circulation or filtration system of automobiles or other vehicles. In that case, the UV-LED air purification system may be implemented as part of the air circulation or filtration at the time of manufacturing of the car air filtration system or may be added later into the car air filtration system.

Figure 1:
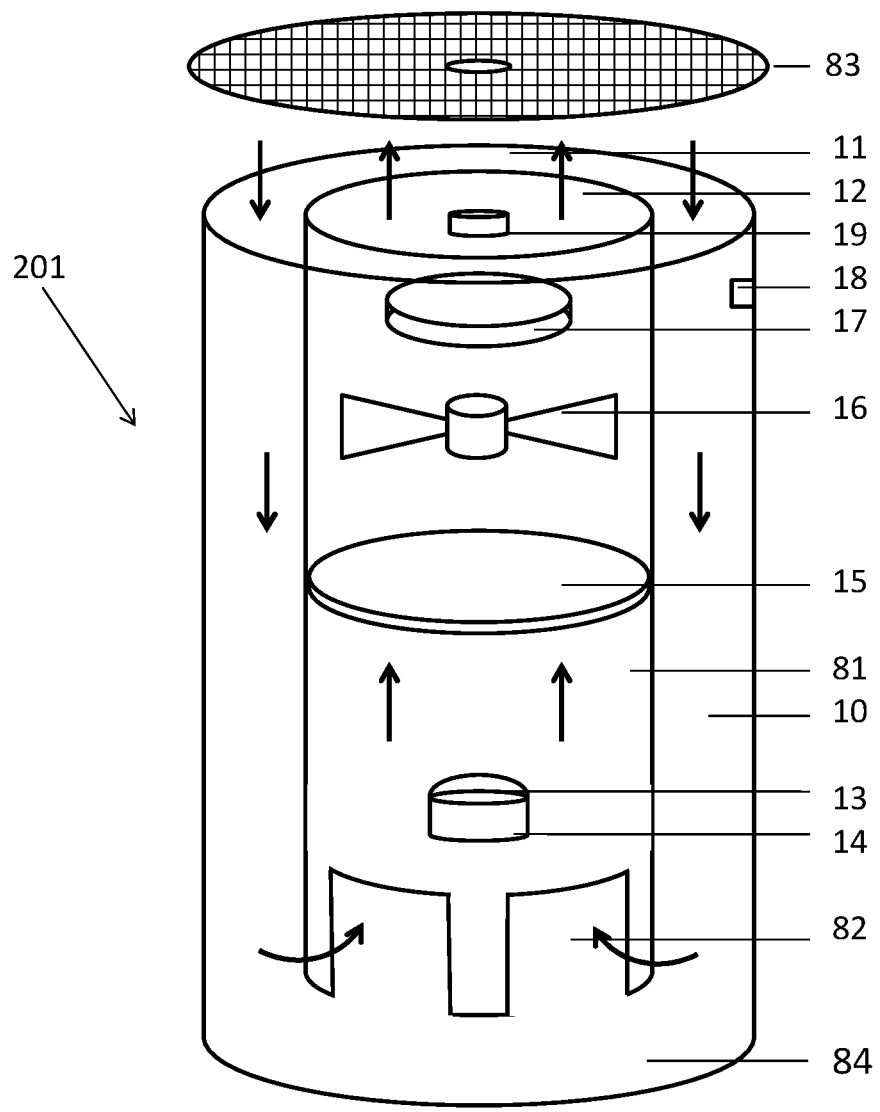
FIG. 1 is a partially-diagrammatic perspective view of a UV-LED air purification system of the present invention.
Figure 2:
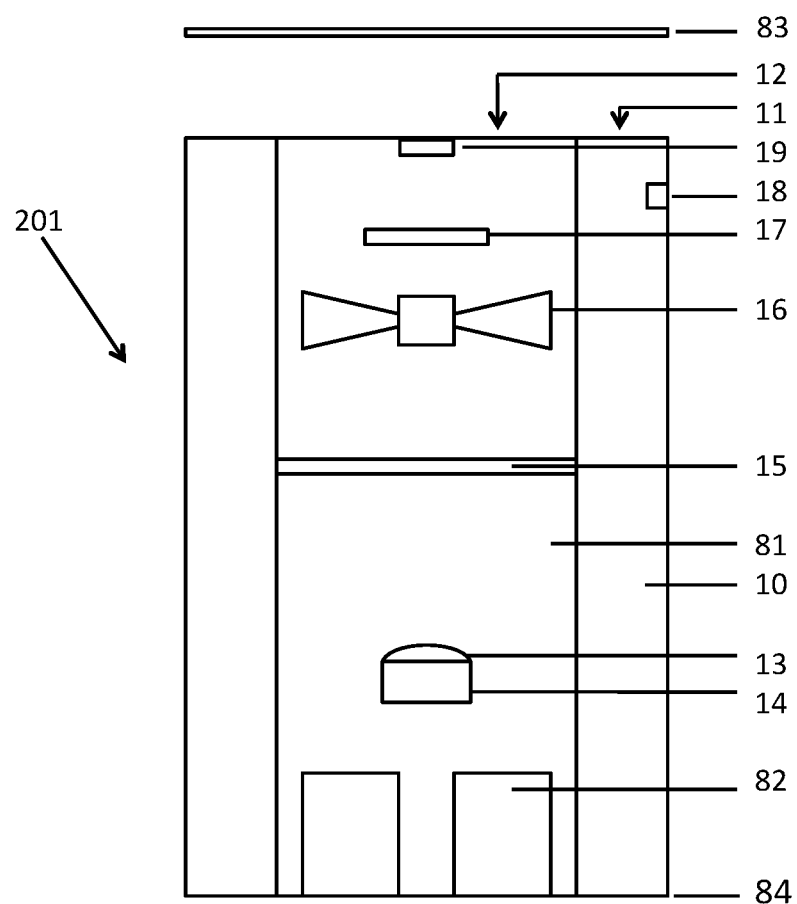
FIG. 2 is a partially-diagrammatic side view of a UV-LED air purification system shown in FIG. 1.
Figure 3:
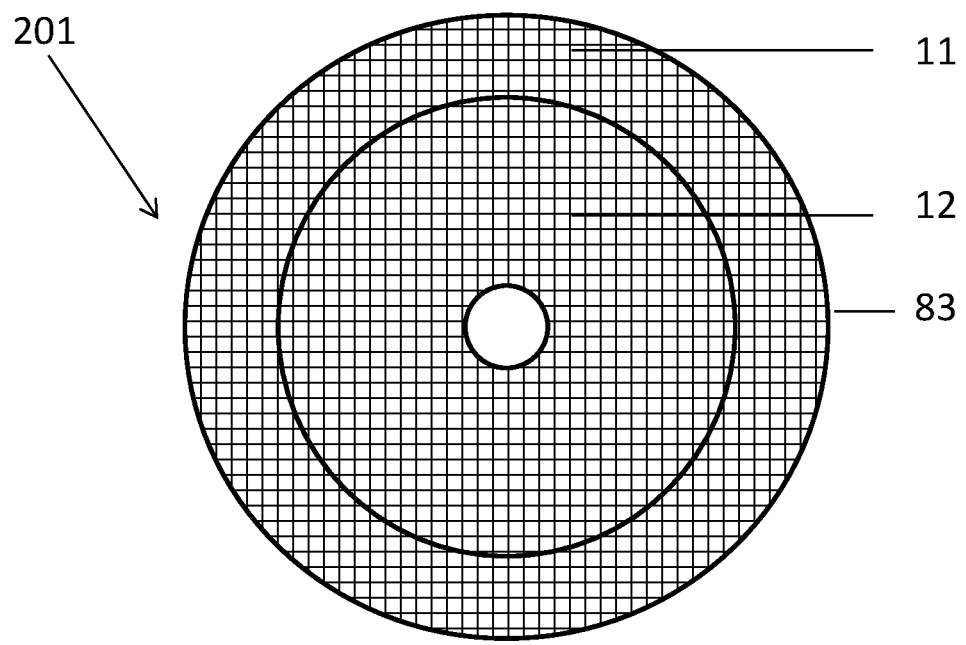
FIG. 3 is a partially-diagrammatic top view of a UV-LED air purification system shown in FIG. 1.

Referring now to FIG. 1 to FIG. 3, an air purification system 201 is shown according to an exemplary embodiment of the present invention. FIG. 1 to FIG. 3 shows a partially-diagrammatic perspective view of air cleaning system 201 having a rigid housing 10, an inlet 11 for airflow to enter and an outlet 12 for airflow to exit, an UV-LED 13 with heat sink 14 to remove the heat generated by the UV-LED, a photocatalyst structure 15, an electrical fan 16, an internal cylinder 81, electrical circuits 17 such as electrical drive circuits for UV-LED and other electronic components operation and microcontrollers for controlling the operation and automation, a power port 18, and an on/off key 19. The internal cylinder 81 is concentrically disposed in the housing 10. The components of the air purification system may be held in their places or may be connected to one another by different means. For example, the LED 13, the photocatalyst structure 15, the electrical fan 16, and the electrical circuits 17 may be held in their places by connecting to the internal cylinder 81. The internal cylinder 81 has openings 82 to allow air to flow through. A perforated cap 83 is used on the inlet and outlet. This is to allow for the airflow movement in and out of the air purifying system, while covering inlet and outlet large openings. A cap 84 is used as the bottom of the system. For a better illustration, the perforated cap 83 is shown as an expanded view (with a distance from the inlet and outlet) in FIG. 1 and FIG. 2. The arrows in FIG. 1 show the overall direction of the airflow moving through the air cleaning system.

Still referring to the air purifying system in FIG. 1 to FIG. 3, the internal cylinder makes possible for the airflow to both enter and exit from the same end (top end, in FIG. 1 to FIG. 3) of the system, allowing the other end (bottom end, in FIG. 1 to FIG. 3) to be placed inside of a holder. Airflow enters the air cleaning system from the inlet 11 and after flowing downward in the annulus between the housing 10 and the internal cylinder 81, it flows upward in the internal cylinder 81 and passes through the pores of a photocatalyst structure 15. The photocatalyst structure may be a photocatalyst immobilized on a porous substrate (such as metal foam) or a perforated substrate (such as mesh). The UV-LED irradiates the photocatalyst; the photocatalyst is activated and initiate the desired reactions for microorganism inactivation and for chemical pollutant degradation in the airflow.

Figure 4:
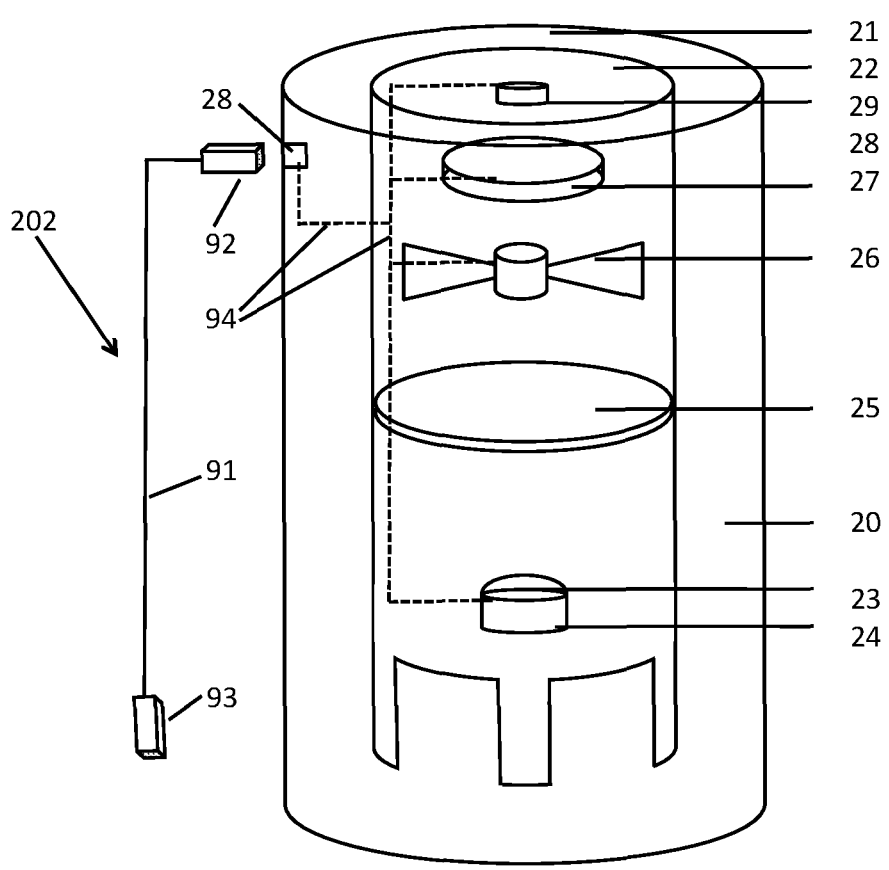
FIG. 4 is a partially-diagrammatic perspective view of a UV-LED air purification system of the present invention.

Referring now to FIG. 4 there is shown a partially-diagrammatic perspective view of an air purification system 202 having a rigid housing 20, an inlet 21 for airflow to enter and an outlet 22 for airflow to exit, an UV-LED 23 with heat sink 24, a photocatalyst structure 25, an electrical fan 26, electrical circuits 27, a power port 28, and an on/off key 29. The air purification system is powered by electricity through a cable 91 with a connector 92 and a plug 93. The plug 93 may be a USB or other plugs, to be connected to a power outlet in an automobile and other vehicles. Still referring to FIG. 4, there are wires and/or other eclectically conductive material 94 in the air purifying system to electrically connect the components. The power port 28, the on/off key 29, the LED 23, and the fan 26 may be connected to drive circuits 27 by wires 94 to control and power the fan and UV LED. The LED, fan, and on/off key may have their separate circuit boards.

Figure 5:
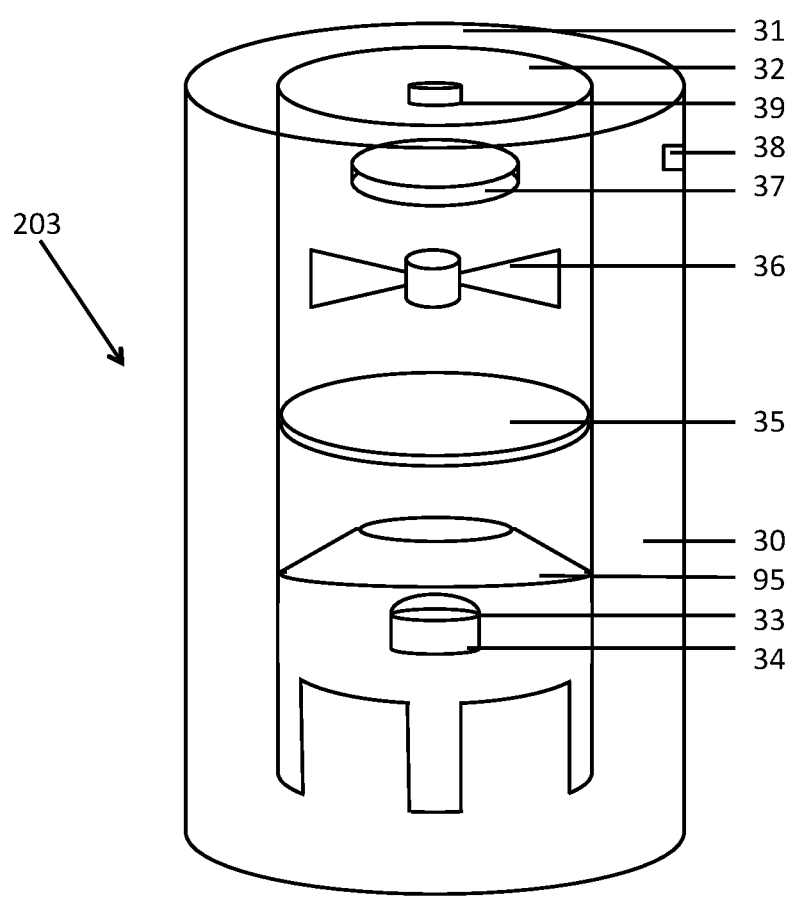
FIG. 5 is a partially-diagrammatic perspective view of a UV-LED air purification system of the present invention.

Referring now to FIG. 5 there is shown a partially-diagrammatic perspective view of an air purification system 203 having a rigid housing 30, an inlet 31 for airflow to enter and an outlet 32 for airflow to exit, a LED 33 with heat sink 34, a photocatalyst structure 35, a fan 36, electrical circuits 37, a power port 38, and an on/off key 39. The air purification system further includes a baffle 95 to better distribute the airflow that flows through the photocatalyst structure, resulting in higher efficiency of the system.

Figure 6:
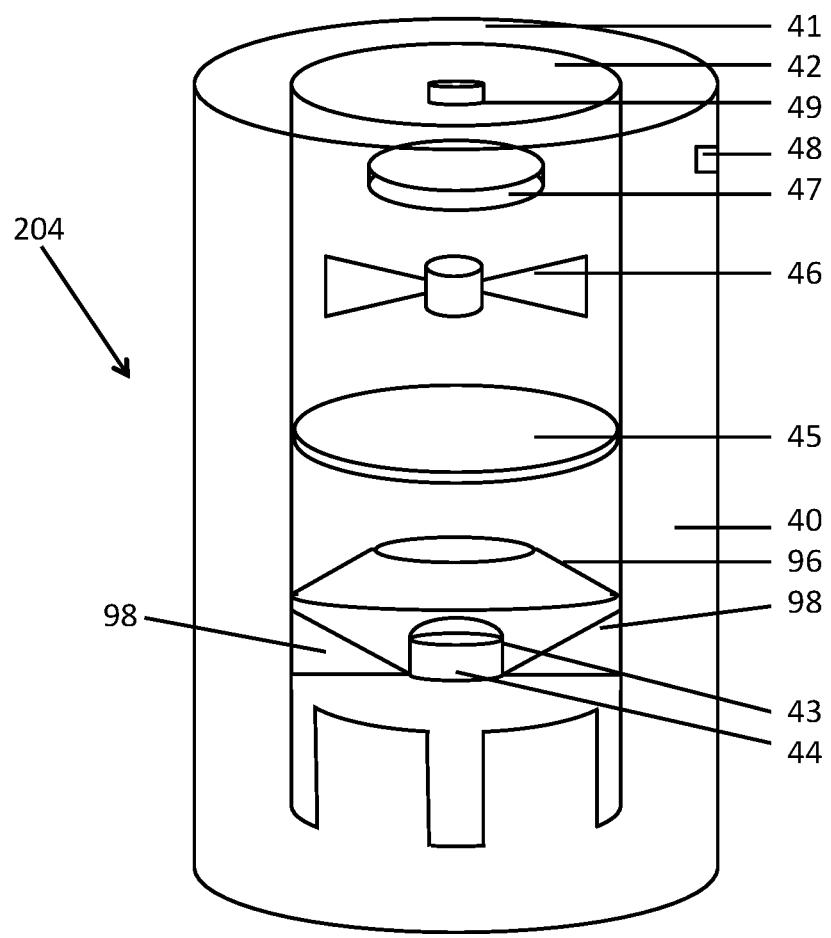
FIG. 6 is a partially-diagrammatic perspective view of a UV-LED air purification system of the present invention.

Referring now to FIG. 6 there is shown a partially-diagrammatic perspective view of an air purification system 204 having a rigid housing 40, an inlet 41 for airflow to enter and an outlet 42 for airflow to exit, a LED 43 with heat sink 44, a photocatalyst structure 45, a fan 46, electrical circuits 47, a power port 48, an on/off key 49, and a baffle 96. The UV-LED board or its heat sink is connected by heat conductive plates 98 to the internal cylinder for better heat transfer and thermal management of the UV-LED.

Figure 7:
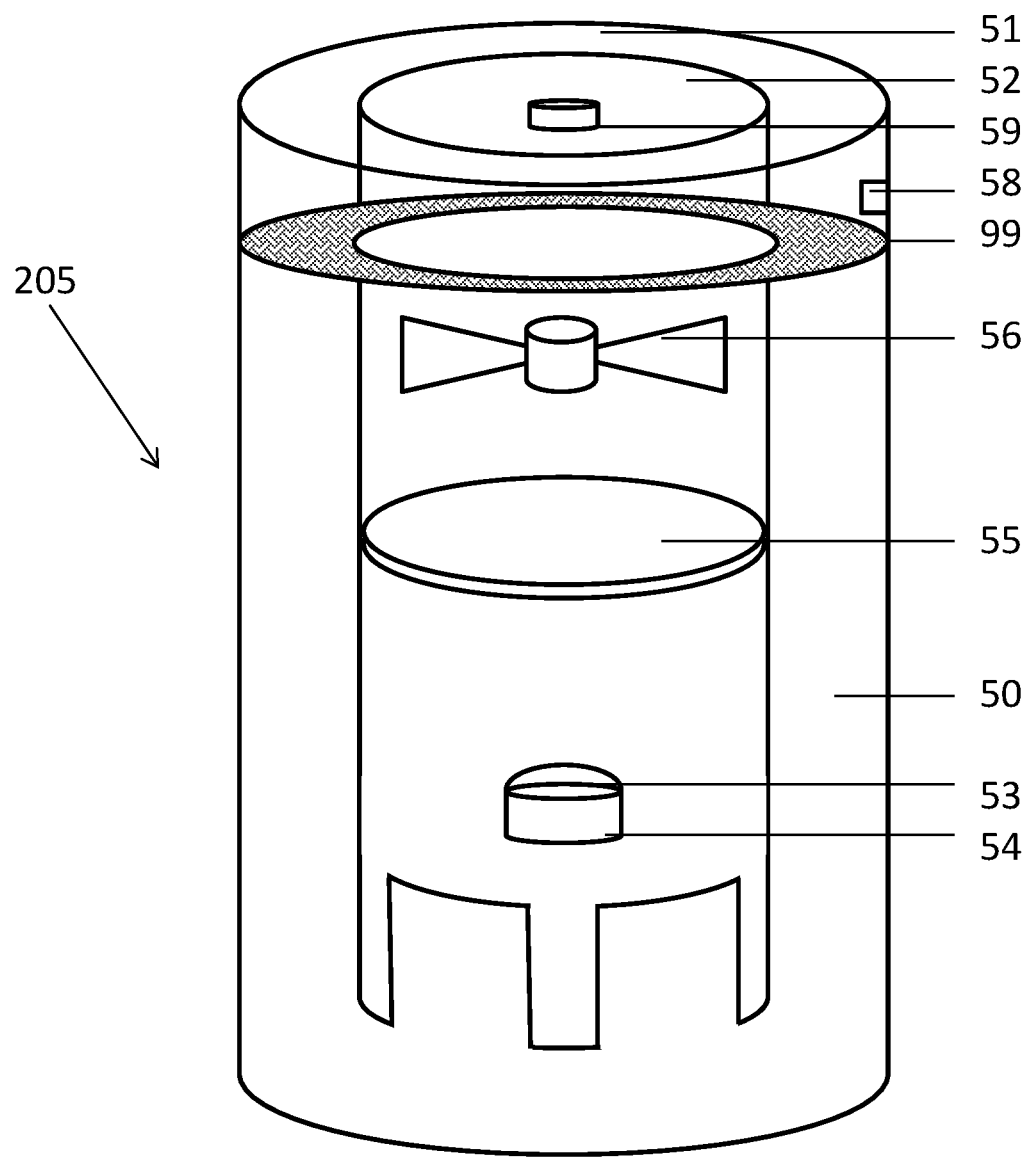
FIG. 7 is a partially-diagrammatic perspective view of a UV-LED air purification system of the present invention.

Referring now to FIG. 7 there is shown a partially-diagrammatic perspective view of an air purification system 205 having a rigid housing 50, an inlet 51 for airflow to enter and an outlet 52 for airflow to exit, a LED 53 with heat sink 54, a photocatalyst structure 55, a fan 56, electrical circuits 57, a power port 58, and an on/off key 59. The air purification system further includes a filter 99 that may be made of carbon or other material or may contain carbon or other material. One or more filters are used to absorb undesirable airborne materials, such as particulate, chemical, and microbial contaminants from the airflow.

Figure 8:
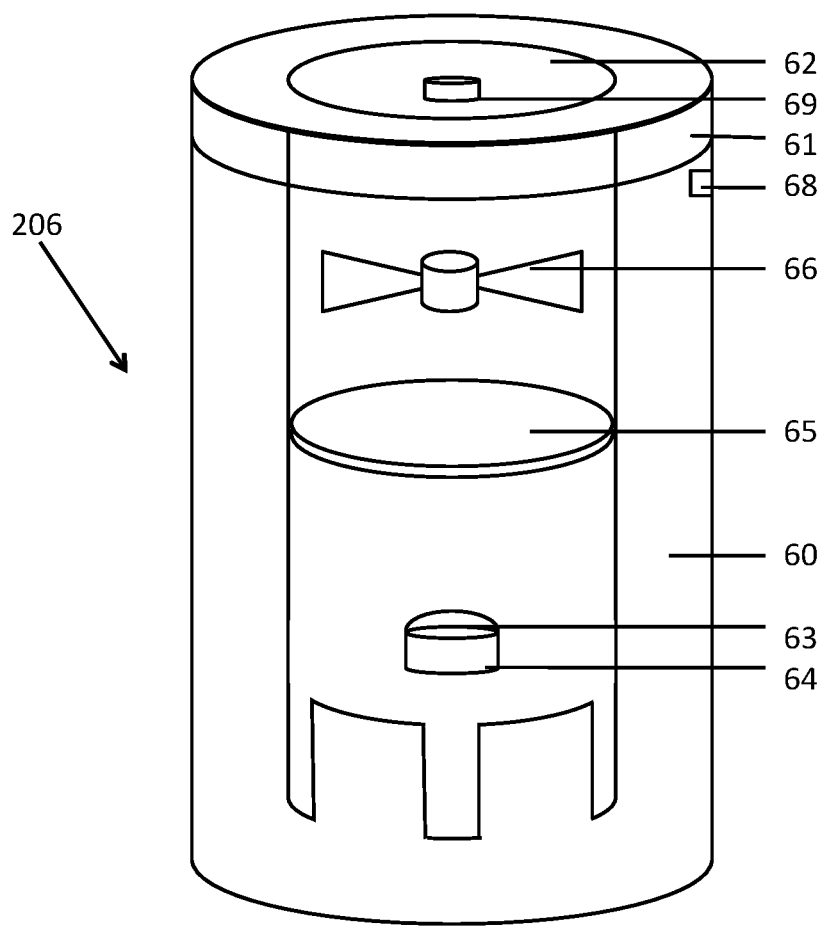
FIG. 8 is a partially-diagrammatic perspective view of a UV-LED air purification system of the present invention.

Referring now to FIG. 8 there is shown a partially-diagrammatic perspective view of an air purification system 206 having a rigid housing 60, an inlet 61 for airflow to enter and an outlet 62 for airflow to exit, a LED 63 with heat sink 64, a photocatalyst structure 65, a fan 66, electrical circuits 67, a power port 68, and an on/off key 69. The inlet 61 is on the side, while the outlet is on the top of the air purification system. The advantage of this configuration is that there is minimal mixing between the untreated airflow entering the inlet and the treated airflow exiting the outlet.

Figure 9:
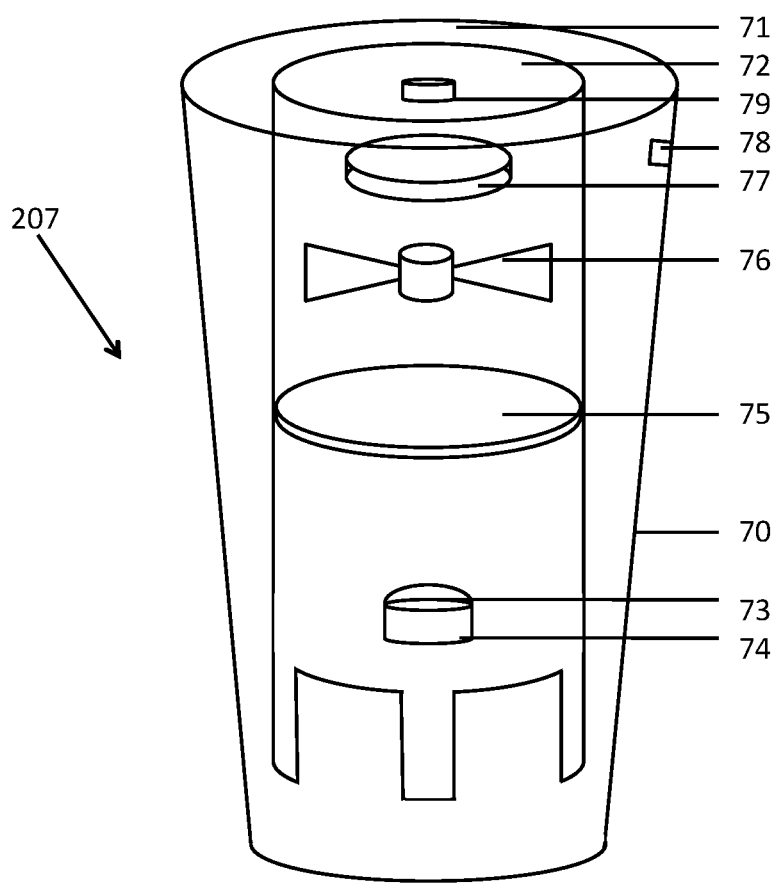
FIG. 9 is a partially-diagrammatic perspective view of a UV-LED air purification system of the present invention.

Referring now to FIG. 9 there is shown a partially-diagrammatic perspective view of an air purification system 207 having a rigid housing 70, an inlet 71 for airflow to enter and an outlet 72 for airflow to exit, a LED 73 with heat sink 74, a photocatalyst structure 75, a fan 76, electrical circuits 77, a power port 78, and an on/off key 79. The UV-LED air purification system has the shape of a conical frustum (as shown in FIG. 9). It may also have the shape of a popular beverage container such as a coffee tumbler, a coffee mug, a coffee cup, a beverage can, and the like. These shapes make it easy for the air purifying system to be placed inside of an automobile cup holder or other holders, and give the system a more familiar look.

In further detail, referring to the invention of FIG. 1 to FIG. 9, the airflow moving in the system removes the heat generated by the LED and other components. When the airflow moves inside the annulus—the space between the system housing and the internal cylinder—, it helps keeping the temperature of the air purifying system's housing low and simultaneously removes the heat generated by the LED in the internal cylinder.

Figure 10:
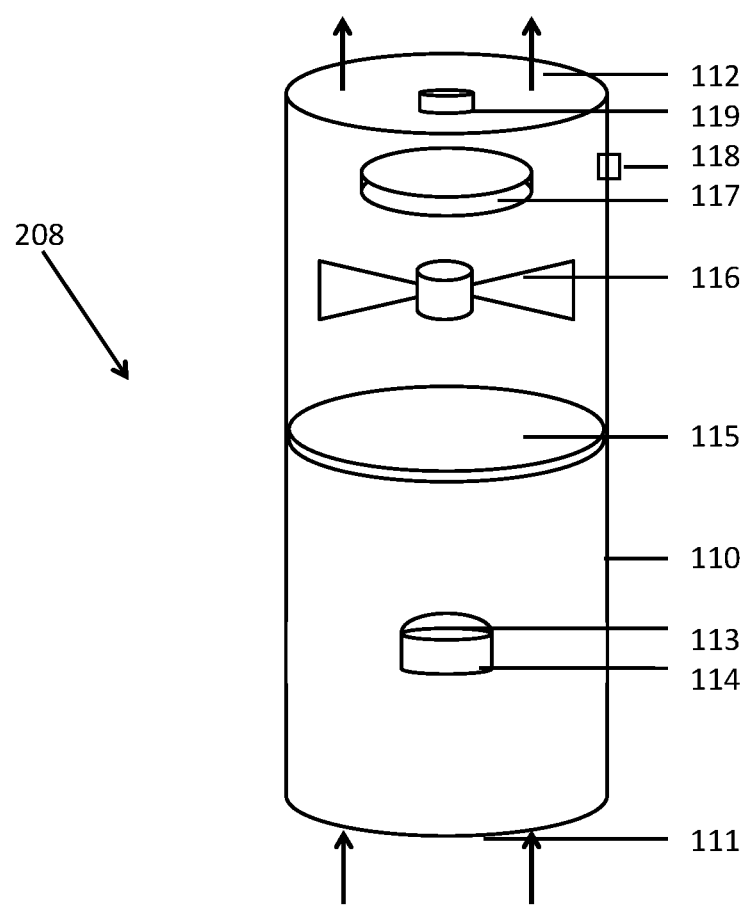
FIG. 10 is a partially-diagrammatic perspective view of a UV-LED air purification system of the present invention.

Referring now to invention shown in FIG. 10, there is shown an air purification system 208 having a rigid housing 110, an inlet 111 for airflow to enter and an outlet 112 for airflow to exit, a LED 113 with heat sink 114, a photocatalyst structure 115, a fan 116, electrical circuits 117, a power port 118, and an on/off key 119. The airflow enters the air purifying system from one end and exit the system from the other end. The arrows show the overall direction of the airflow moving through the system. The air purifying system configuration shown in FIG. 10 may be integrated into the air circulation or air ventilation pipe (preferably the main pipe) of a vehicle cabin, for cleaning the air entering to the cabin.

Figure 11:
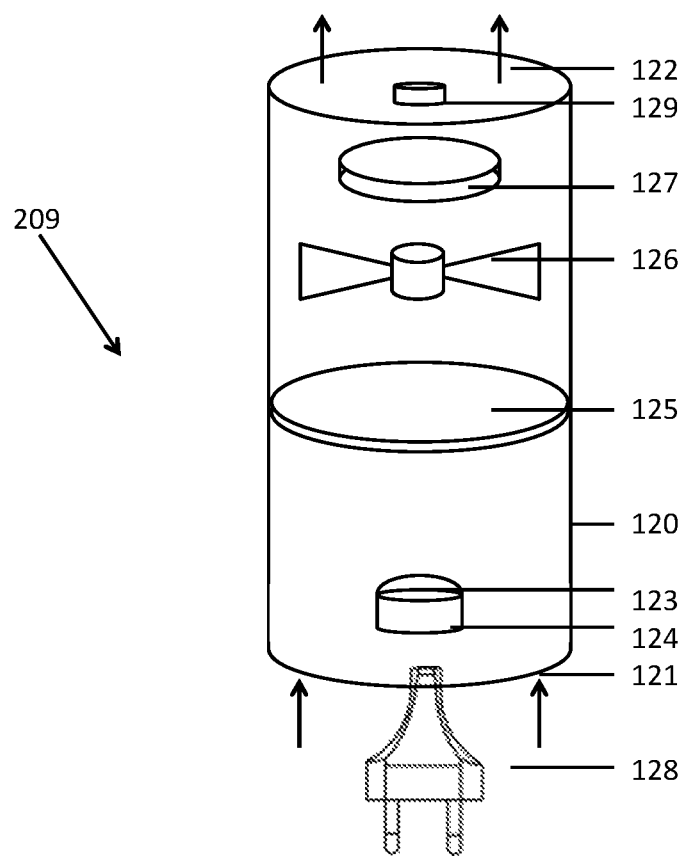
FIG. 11 is a partially-diagrammatic perspective view of a UV-LED air purification system of the present invention.

Referring now to the invention shown in FIG. 11, there is shown an air purification system 209 having a rigid housing 120, an inlet 121 for airflow to enter and an outlet 122 for airflow to exit, a LED 123 with heat sink 124, a photocatalyst structure 125, a fan 126, electrical circuits 127, and an on/off key 129. The air purification system, which is sufficiently small, has a rigid power connector or plug 128 attached to its housing that may be directly connected to a power outlet in an automobile and other vehicles. The arrows show the overall direction of the airflow moving through the air purifying system.

Referring to the air purification system of FIG. 1 to FIG. 11, the shape of the air purification system housing (e.g. 10, in FIG. 1) may be different. The shape, position, orientation, order, and dimensions of LED, photocatalyst, fan, and other internal and external components may be different. The shape, position, and location of inlet (e.g. 11, in FIG. 1) and outlet (e.g. 12, in FIG. 1) may vary. Still referring to the air purification system of FIG. 1 to FIG. 11, more than one LED and photocatalyst structure may be inside the air purification system. More than one set of LED and photocatalyst may be stacked in the air purification system. Also, the photocatalyst may be irradiated from one side or both sides by LEDs. The LED (e.g., 13, FIG. 1) may have a range of power outputs and wavelengths suitable for photocatalyst activation. The wavelength peak of the LED may be in UV radiation range, including wavelength from 250 nm to 385 nm. Still referring to the air purification system of FIG. 1 to FIG. 11, the photocatalyst may be unsupported structure or be supported on a substrate structure. The photocatalyst structure may be a perforated, porous, solid or other material; its shape may be flat, dome, and the like, where airflow flows through and/or over the photocatalyst structure. Still referring to the air purification system of FIG. 1 to FIG. 11, the drive (e.g. 17 in FIG. 1) may be designed such that the air purifying system and LED is powered with different power sources including a battery and/or electrical plug and/or solar cell, and/or other power sources. Also, the air purification system may have its power source integrated in the system, such as a replaceable battery, a rechargeable battery and the like.

The construction details of the invention as shown in FIG. 1 to FIG. 11, are that the system housing may be made of aluminum, stainless steel, or of any other sufficiently rigid and strong material such as metal, alloy, high-strength plastic, and the like. The inlet and outlet caps may be made of any perforated material, mesh, and the like. Further, the various components of the air purification system may be made of different materials. For example, the conductive plates (e.g., 98, FIG. 6) may be made of copper, aluminum, or other heat conductive material. The photocatalyst support substrate may be a porous material such as a mesh or foam made of metal or metal composite or metal alloy, or other material. The housing may be made of material double layer with vacuum insulation (between the layers).

The parts of the invention as shown in FIG. 1 to FIG. 11 may be put together in several ways. For example, the main components, including the LED and photocatalyst may be connected on a frame that fits inside the air purification system housing. The housing mat be closed on one side (top or bottom) or both sides (top and bottom) by a cap. The cap, if used as inlet and outlet cover, may have several openings to allow airflow to flow through the air purifying system; it may also be made of perforated material or mesh structure to allow the flowing of the airflow in and out of the system. The air purifying system may be easily opened and closed, for example by removing, unlocking, or unscrewing the cap on one or both sides (top and bottom). The air purifying system components, including the UV-LED and photocatalyst structure, may be easily replaceable. For example, the photocatalyst structure may slide in and out from an opening (e.g. slot) on the side of the internal cylinder.

Figure 12A:
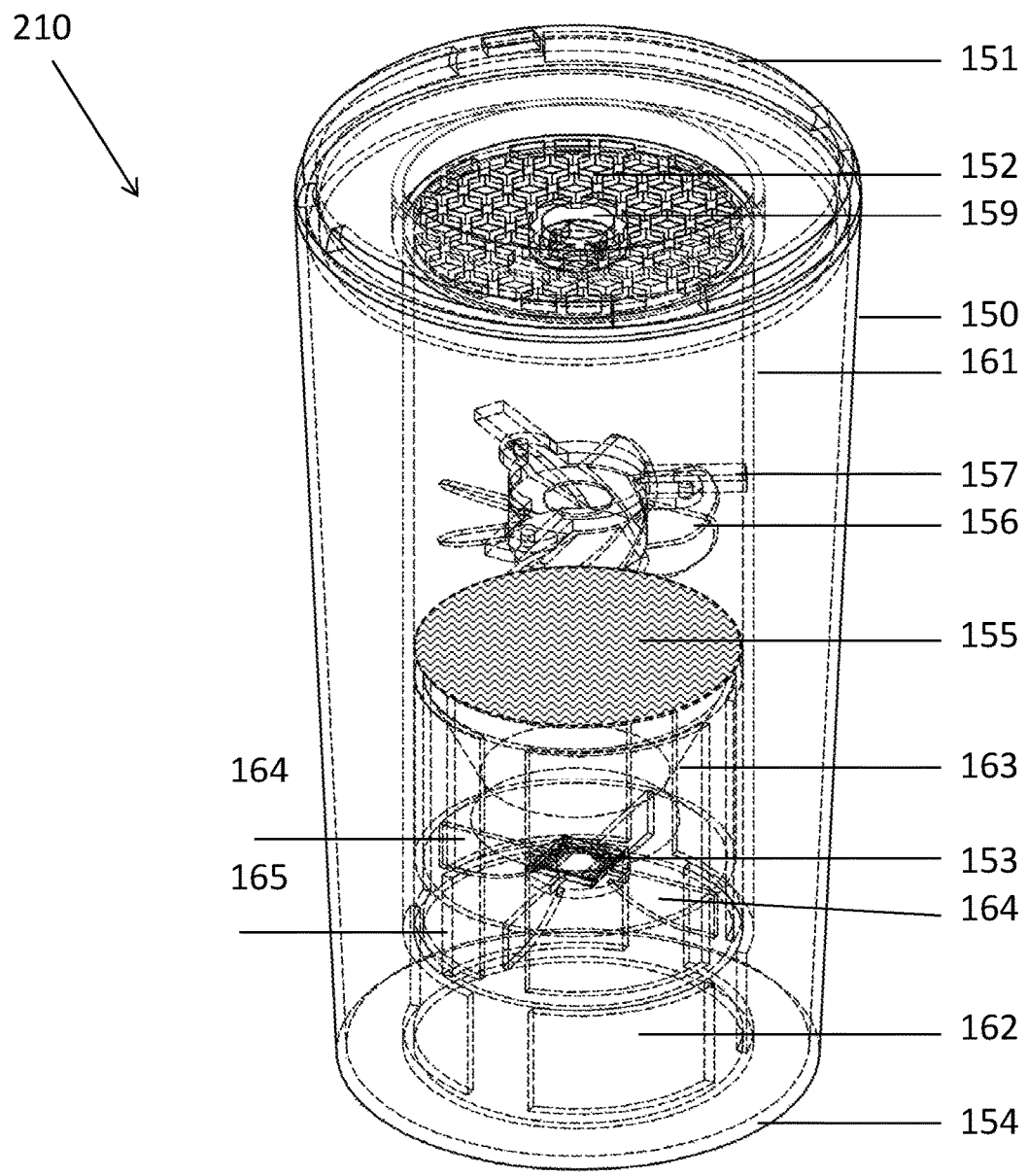
FIGS. 12A-12C is a partially-diagrammatic perspective view (12A), top view (12B), and side view (12C) of a UV-LED air purification system of the present invention.
Figure 12B:
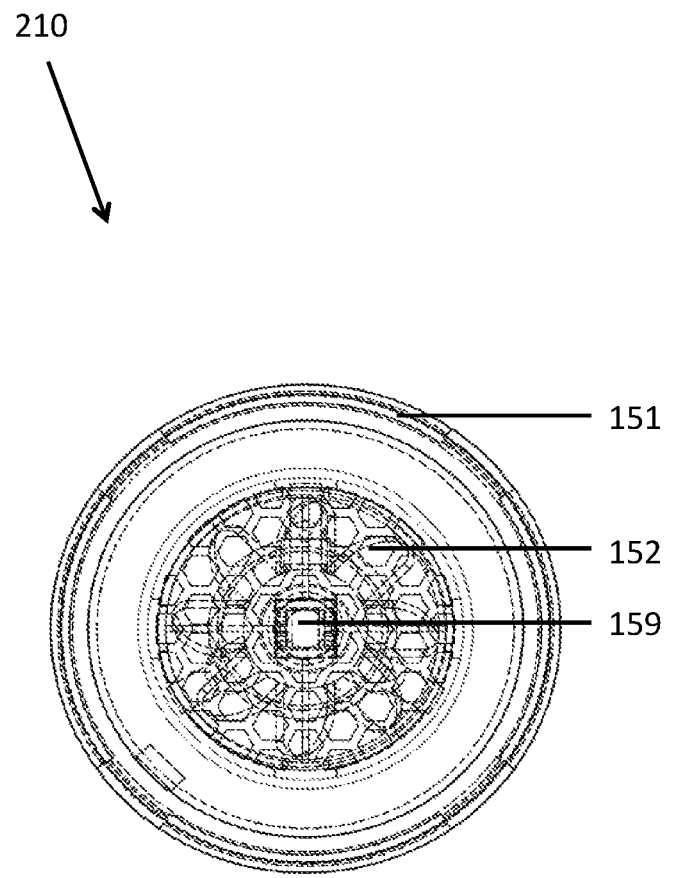
Figure 12C:
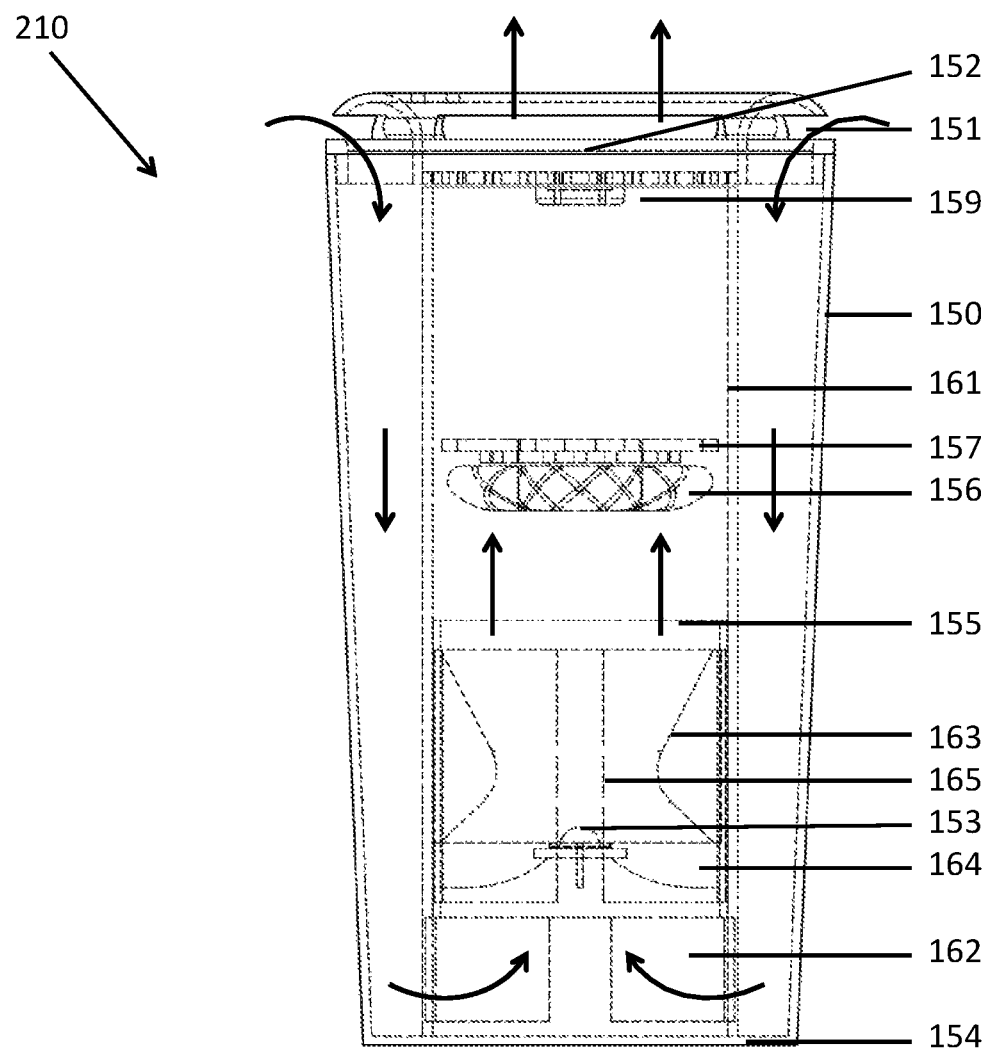

Referring now to the invention shown in more detail in FIGS. 12A-12C, there is shown partially-diagrammatic perspective view (FIG. 12A), top view (FIG. 12B), and side view (FIG. 12C) of an air purification system 210. In FIGS. 12A-12C the invisible parts are mainly shown by broken lines. In FIGS. 12A-12C, there is shown an air purification system 210, having a rigid housing 150, an inlet 151 for airflow to enter, an outlet 152 covered by a perforated cap for airflow to exit, a bottom 154, an internal cylinder 161 with openings 162 for airflow to go through, an UV-LED 153, a photocatalyst structure 155, an electrical fan 156, prolongs 157 to connect the fan to the internal cylinder 161, an on/off key 159, a baffle 163 having the shape of a "hyperboloid of one sheet", thermal conductive plates 164, and a frame 165 for connecting the LED, the baffle, and the photocatalyst. The drive circuits (not shown) for operating the UV-LED and other electrical components may be placed in the space between the fan 156 and on/off key 159, preferably in the central space, not to block the airflow. The UV-LED drive circuit (not shown) may alternatively be placed under the UV-LED 153. The UV-LED may be connected to a heat sink (not shown) for its thermal management.

Still referring to the invention shown in FIG. 12A-12C, the internal cylinder 161 makes possible for the airflow to both enter and exit from the same end (top) of the system. Further, the internal cylinder 161 provides a housing for holding some of the air purifying system components including the photocatalyst structure 155, UV-LED 159, fan 156, and baffle 163. The inlet 151 is consisting of several opening slots on the side of the air purification housing at the top-end, and the outlet 152 is on the top of the air purification system. This configuration minimizes mixing between the untreated airflow entering the inlet 151 (mainly horizontally from the top side area) and the treated or purified airflow exiting the outlet 152 (mainly vertically from the top central area), as shown in FIG. 12C by the arrows. Still referring to FIGS. 12A-12C, the air purification system 150 has the shape of a coffee tumbler to be easily placed inside of an automobile cup holder and to have a familiar look. The arrows in FIG. 12C show the overall direction of the airflow moving through the air purifying system.

Figure 13:
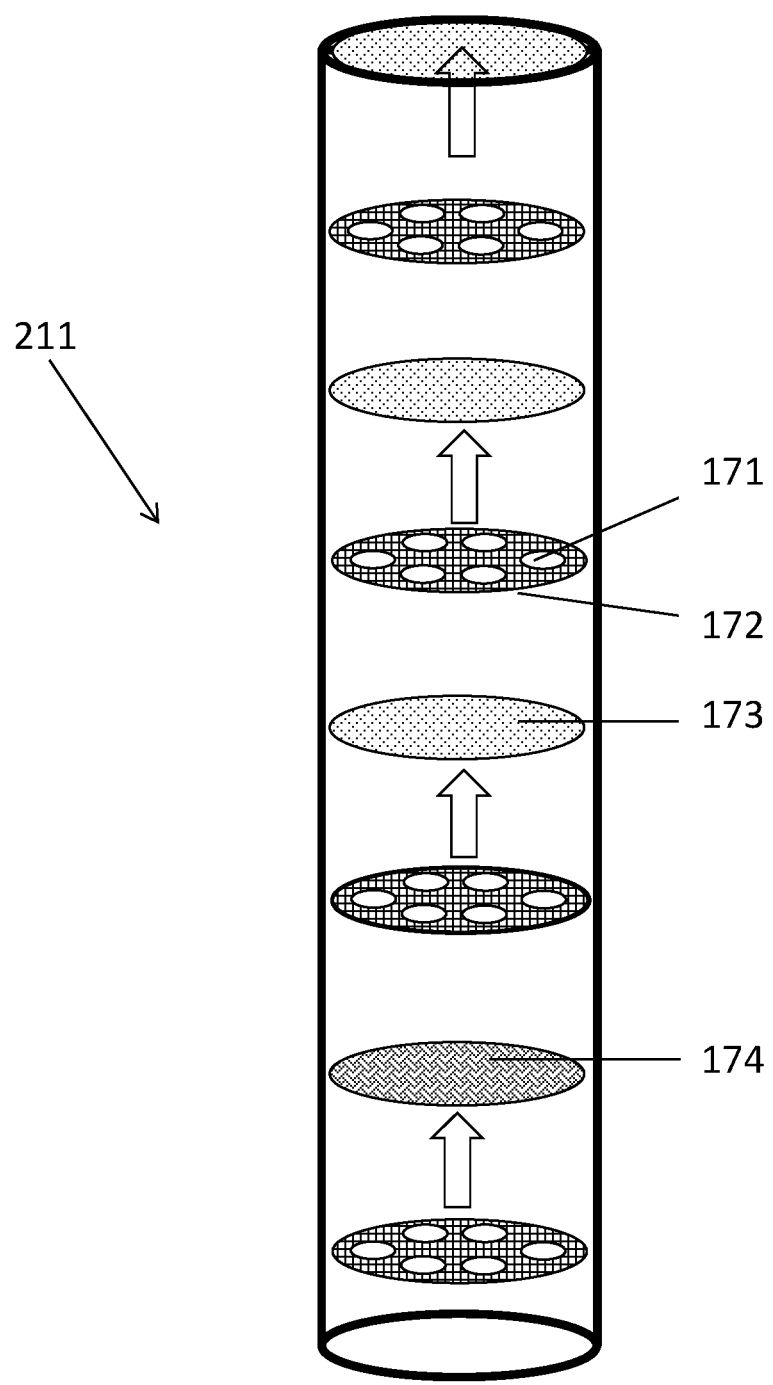
FIG. 13 is a partially-diagrammatic perspective view of a conceptual design of a UV-LED air purification system of the present invention.
Figure 14:
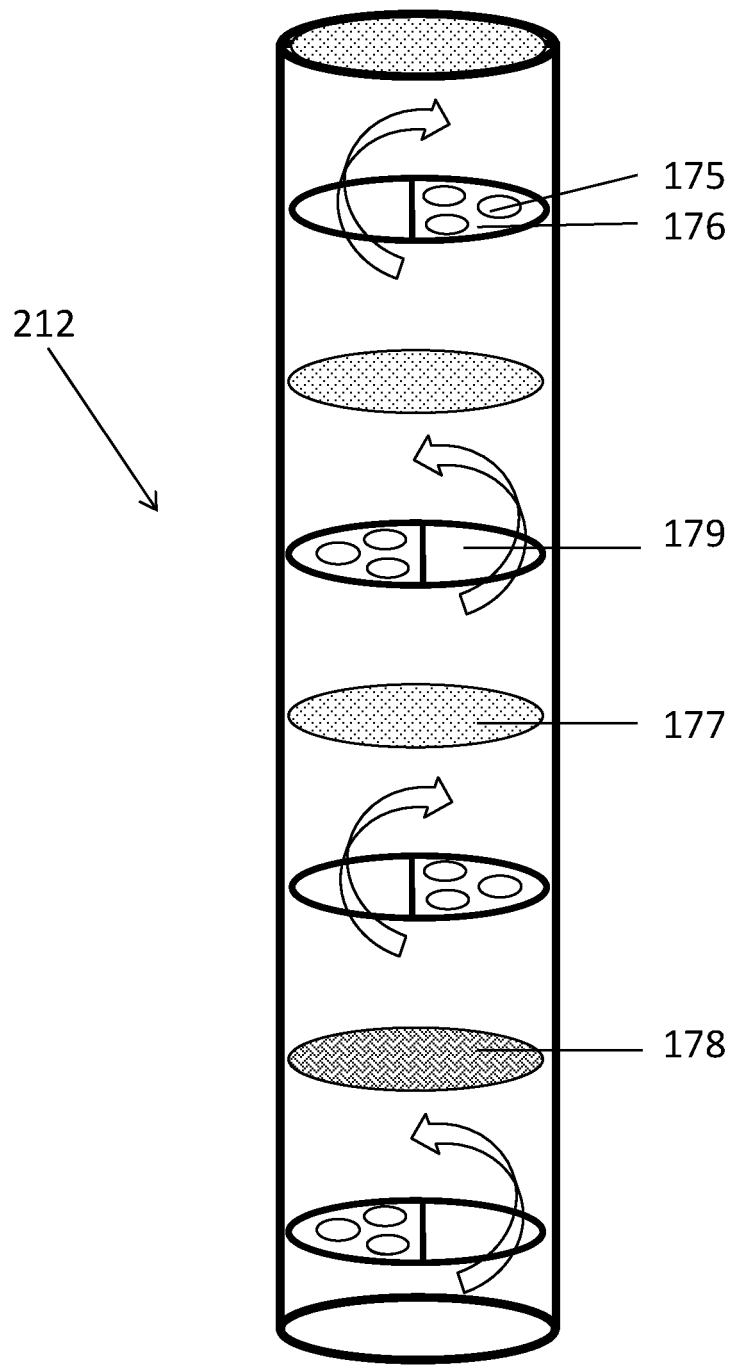
FIG. 14 is a partially-diagrammatic perspective view of a conceptual design of a UV-LED air purification system of the present invention.

Referring now to FIG. 13 and FIG. 14, there are shown two potential configurations for UV-LEDs and photocatalyst structure arrangements in an air purification system with multi UV-LEDs and multi photocatalyst structures and a filter. Only the UV-LEDs, photocatalysts, and filter parts of the air purifying system are shown in these figures (for simplicity and for a better illustration of the concepts).

Referring now to FIG. 13, there is shown a partially-diagrammatic perspective view of a configuration for UV-LEDs and photocatalyst structure arrangements in an air purification system 211, having a series of UV-LEDs 171 mounted on perforated boards 172, and a series of photocatalyst structures 173, and a filter 174, wherein the photocatalyst structures and the filter are irradiated by the UV-LEDs. Airflow passes through the LED perforated boards, photocatalyst structures, and the filter. The filter is irradiated by UV radiation from UV-LED to inactivate microbial contaminates and to degrade organic pollutants absorbed on the filter that may be eliminated by direct photolysis, without the need for photocatalytic reactions. The arrows show the overall direction of the airflow flowing through the UV-LEDs and photocatalyst structures.

Referring now to FIG. 14, there is shown another partially-diagrammatic perspective view of a configuration for UV-LEDs and photocatalyst structure arrangements in an air purification system 212, having a series of UV-LEDs 175 mounted on solid boards 176, and a series of photocatalyst structures 177, and a filter 178, wherein the photocatalyst structures and the filter are irradiated by the UV-LEDs. Airflow (shown by the arrows) passes through the open-side of the LED boards 179 and through the photocatalyst structures and the filter. This design may enhance the flow mixing through the air purifying system. The arrows show the overall direction of the airflow flowing through the UV-LEDs and photocatalyst structures.

In both air purification system configurations presented in FIG. 13 and FIG. 14, the photocatalyst structures may be irradiated by UV-LEDs from one side or both sides. Further, in both configurations presented in FIG. 13 and FIG. 14, static mixers (not shown) or baffles (not shown) may be used to enhance the airflow hydrodynamics and to enhance mass transfer of chemical contaminants to and from the photocatalyst surface.

The advantages of the present invention include, without limitation, that it is a portable, compact air purifying system that can be easily placed inside vehicles. Further, the system purifies airflow by both inactivation of microorganisms and degradation of many chemical pollutants. Further, the system can be operated at low voltage and low power, unlike many other electronic air purification systems. Further, the system can be easily operated by several power sources, including a vehicle battery. Further, the system can be a stand-alone device or be integrated into a vehicle air circulation system. Further, if the system is a stand-alone device, it can be easily placed in a typical cup holder, which is commonly found in many vehicles, such as automobiles.

In broad embodiment, the present invention is a compact air purifying system operating with photocatalyst activated by UV-LED applicable to air treatment in vehicles.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:
1. An air purification system comprising:
   a housing, the housing elongated in an axial direction and having an inlet for permitting air to be purified to enter an interior of the housing and outlet for permitting purified air to be exhausted from the interior of the housing and the housing defining an air-flow path through which an airflow is capable of moving between the inlet and the outlet, a portion of the air-flow path elongated in the axial direction and shaped so that the airflow capable of moving within the portion of the air-flow path flows in the axial direction;
   an ultraviolet light emitting diode (UV-LED) supported within the interior of the housing and arranged to emit ultraviolet (UV) radiation into the portion of the air-flow path with an optical axis of the UV-LED and corresponding UV radiation having a directional component oriented substantially in the axial direction;
   a photocatalyst structure supported in a central region of the portion of the air-flow path where it is positioned to be irradiated by the UV radiation from the UV-LED and where the airflow is capable of flowing in the axial direction toward the photocatalyst structure on an inlet side of the photocatalyst structure and where the airflow is capable of flowing in the axial direction away from the photocatalyst structure on an outlet side of the photocatalyst structure, the inlet side opposing the outlet side, the photocatalyst structure comprising a photocatalyst;
   one or more flow-shaping elements, each flow-shaping element supported in the air-flow path and shaped to provide at least one airflow guiding surface, wherein at least a portion of the airflow guiding surface extends from a location downstream of the UV-LED to a location upstream of the photocatalyst structure for directing the airflow toward the inlet side of the photocatalyst structure; and
   wherein the UV-LED is arranged to emit radiation directed toward the inlet side of the photocatalyst structure.

2. The air purification system of claim 1, further comprising a plurality of ultraviolet light emitting diodes (UV-LEDs), each of the UV-LEDs supported within the interior of the housing.

3. The air purification system of claim 2, wherein each of the plurality of UV-LEDs is capable of emitting radiant power at a corresponding peak wavelength and at least two of the corresponding peak wavelengths are different from one another.

4. The air purification system of claim 1, further comprising a plurality of photocatalyst structures supported within the air-flow path, wherein each of the plurality of photocatalyst structures comprises a different photocatalyst.

5. The air purification system of claim 1 wherein the photocatalyst structure comprises a three-dimensional porous foam structure comprising solid material which defines three-dimensional pores, the three-dimensional pores interconnected for permitting air flow through the photocatalyst structure.

6. The air purification system of claim 1, wherein the one or more flow-shaping elements comprise one or more baffles supported in the air-flow path, each of the one or more baffles shaped to define an air-flow aperture through which air is permitted to flow, the air-flow aperture symmetric about an air-flow axis that extends through the cross-sectional center of the portion of the air-flow path in the axial direction.

7. The air purification system of claim 1 wherein the housing comprises two ends spaced apart from one another in the axial direction, wherein the inlet and the outlet are both located at one of the two ends and wherein the outlet has a first cross-sectional shape and the inlet has a second cross-sectional shape that surrounds a perimeter of the first-cross-sectional shape.

8. The air purification system of claim 1, wherein an exterior of the housing has a circular cross-section and is sized to be received in a vehicle cup holder.

9. A method of purifying air, the method comprising:
creating an airflow in an axial direction through an air-flow path of a reactor, the air-flow path elongated in the axial direction;
locating an ultraviolet light emitting diode to emit ultraviolet (UV) radiation in the air-flow path with an optical axis of the UV-LED and corresponding UV radiation having a direction component oriented substantially in the axial direction;
locating a photocatalyst structure in a central region of the air flow path such that the airflow flows in the axial direction toward the photocatalyst structure on an inlet side of the photocatalyst structure and where the air-flow flows in the axial direction away from the photocatalyst structure on an outlet side of the photocatalyst structure, the outlet side opposing the inlet side;
activating the photocatalyst with UV radiation emitted from the UV-LED;
locating one or more flow-shaping elements in the air-flow path, each flow-shaping element shaped to provide at least one airflow guiding surface, wherein at least a portion of the airflow guiding surface extends from a location downstream of the UV-LED to a location upstream of the photocatalyst structure for directing the airflow toward the inlet side of the photocatalyst structure; and
wherein the UV-LED is arranged to emit radiation directed toward the inlet side of the photocatalyst structure.

10. The air purification system of claim 1 comprising an air moving device, supported in the interior of the housing for creating the airflow from the inlet to the outlet, the air-moving device oriented such that the airflow in the portion of the air-flow path is in the axial direction and the air-moving device located between the outlet and the photocatalyst structure such that the airflow flows in the axial through the photocatalyst structure before reaching the air-moving device and is exhausted from the interior of the of the housing through the outlet after passing through the air-moving device.

11. The air purification system of claim 6 wherein each of the one or more baffles comprises a baffle body, the baffle body symmetric about the air-flow axis.

12. The air purification system of claim 11 wherein the baffle body of at least one of the one or more baffles has a frusto-conical shape.

13. The air purification system of claim 11 wherein the baffle body of at least one of the one or more baffles has a one-sheeted hyperboloid shape.

14. The air purification system of claim 7 wherein the first cross-sectional shape is circular and the second cross-sectional shape is annular.

15. The air purification system of claim 7 wherein the inlet and outlet are shaped such that the perimeter of the first cross-sectional shape defines a portion of the inlet.

16. The air purification system of claim 1 comprising one or more thermally-conducting members in thermal contact with the UV-LED and with one or more walls that define the portion of the air-flow path.

17. The air purification system of claim 16 wherein the one or more thermally-conducting members comprise a plurality of thermally-conducting members which are spaced apart from one another to permit the airflow through one or more spaces therebetween, each of the plurality of thermally-conducting members in thermal contact with the UV-LED and with one or more walls that define the portion of the air-flow path.

18. A method according to claim 9, wherein locating one or more flow-shaping elements in the air-flow path comprises locating a baffle in the air-flow path, the baffle shaped to define an air-flow aperture through which air is permitted to flow, the air-flow aperture symmetric about an air-flow axis that extends through the cross-sectional center of air flow path in the axial direction.

19. A method according to claim 18 wherein the baffle comprises a baffle body that is symmetric about the air-flow axis.

20. A method according to claim 9 wherein creating the airflow comprises introducing air to be purified into the air-flow path through an inlet and exhausting purified air from the air-flow path through an outlet and wherein the outlet has a first cross-sectional shape and the inlet has a second cross-sectional shape that surrounds a perimeter of the first cross-sectional shape.

21. The air purification system of claim 5, wherein the three-dimensional porous foam structure comprises a metal foam fabricated from at least one of: metal, metal composite and metal alloy.

22. A method according to claim 9 wherein the photocatalyst structure comprises a three-dimensional porous foam structure comprising solid material which defines three-dimensional pores, the three-dimensional pores interconnected for permitting air flow through the photocatalyst structure.

* * * * *